(12) United States Patent
Ishiwata (10) Patent No.: US 9,549,791 B2
(45) Date of Patent: Jan. 24, 2017

(54) IMPLANT BODY, METHOD OF MANUFACTURE OF SAME, AND DENTAL IMPLANT

(71) Applicant: Nanto Seimitsu Co., Ltd., Shizuoka (JP)

(72) Inventor: Teruo Ishiwata, Shizuoka (JP)

(73) Assignee: Nanto Seimitsu Co., Ltd., Shizuoka (JP)

( * ) Notice: Subject to any disclaimer, the term of this patent is extended or adjusted under 35 U.S.C. 154(b) by 433 days.

(21) Appl. No.: 14/254,981

(22) Filed: Apr. 17, 2014

(65) Prior Publication Data

US 2014/0227663 A1 Aug. 14, 2014

Related U.S. Application Data

(62) Division of application No. 12/995,233, filed as application No. PCT/JP2009/060303 on May 29, 2009, now abandoned.

(30) Foreign Application Priority Data

May 30, 2008 (JP) ................................. 2008-143883
May 23, 2009 (JP) ................................. 2009-124780

(51) Int. Cl.
  *A61C 8/00* (2006.01)
  *A61C 13/00* (2006.01)
  (Continued)

(52) U.S. Cl.
  CPC ........... *A61C 8/0015* (2013.01); *A61C 8/0012* (2013.01); *A61C 8/0013* (2013.01);
  (Continued)

(58) Field of Classification Search
  CPC ........................... A61C 8/0012; A61C 8/0015
  (Continued)

(56) References Cited

U.S. PATENT DOCUMENTS 4,983,182 A   1/1991 Kijima et al.
5,062,798 A   11/1991 Tsuge et al.
(Continued)

FOREIGN PATENT DOCUMENTS

EP   1825830 A1   8/2007
JP   63-105764 S   5/1988
(Continued)

OTHER PUBLICATIONS

Yen et al., "Characterization of Electrolytic ZrO2 Coating on Co—Cr—Mo Implant Alloys of Hip Prosthesis", Biomaterials, 2001, pp. 125-133.
(Continued)

*Primary Examiner* — Cachet Sellman
(74) *Attorney, Agent, or Firm* — Carter, DeLuca, Farrell & Schmidt, LLP (57) ABSTRACT

To obtain improved bio-affinity and high bone attachment in an implant body, a method of manufacture for the implant body, and a dental implant. The implant body is fixed in a contact configuration to bone, and includes the base material formed from zirconia, and a surface layer formed on the surface of the base material and having a lower hardness than the base material. Therefore, in addition to having superior mechanical strength due to the zirconia base material, the soft and flexible surface layer functions as a buffer layer to mitigate the difference in the degree of hardness between the bone and the base material, and therefore the soft surface further improves the bone adhesion characteristics.

12 Claims, 6 Drawing Sheets

(51) Int. Cl.
A61K 6/02 (2006.01)
A61L 27/30 (2006.01)
A61L 27/10 (2006.01)

(52) U.S. Cl.
CPC .......... *A61C 13/0018* (2013.01); *A61K 6/024* (2013.01); *A61L 27/10* (2013.01); *A61L 27/306* (2013.01); *A61C 8/0022* (2013.01); *A61L 2420/02* (2013.01); *A61L 2430/02* (2013.01); *A61L 2430/12* (2013.01); *A61L 2430/24* (2013.01); *A61L 2430/38* (2013.01)

(58) Field of Classification Search
USPC ............. 427/2.24, 2.26, 2.28, 553, 554, 508
See application file for complete search history.

(56) References Cited

U.S. PATENT DOCUMENTS

| | | | |
|---|---|---|---|
| 6,749,653 B2 | 6/2004 | Castro et al. | |
| 6,974,323 B2 | 12/2005 | Weigl et al. | |
| 7,762,814 B2 | 7/2010 | van der Zel | |
| 2004/0083006 A1* | 4/2004 | Ellingsen | A61L 27/58 623/23.57 |
| 2005/0147942 A1* | 7/2005 | Hall | A61C 8/0018 433/173 |
| 2006/0286140 A1 | 12/2006 | Wickstrom et al. | |
| 2007/0202466 A1* | 8/2007 | Schwarz | A61C 8/0012 433/174 |
| 2008/0071358 A1 | 3/2008 | Weber et al. | |

FOREIGN PATENT DOCUMENTS

| | | | | |
|---|---|---|---|---|
| JP | 2-82966 | A | 3/1990 | |
| JP | 10-174694 | A | 6/1998 | |
| JP | EP 1297853 | A1 * | 4/2003 | ............. A61L 27/04 |
| JP | 2007-229463 | A | 9/2007 | |
| JP | 2007229469 | A | 9/2007 | |
| KR | 1020040039802 | A | 5/2004 | |
| WO | 03/086495 | A1 | 10/2003 | |
| WO | 2007/039206 | A1 | 4/2007 | |
| WO | 2008/060451 | A2 | 5/2008 | |

OTHER PUBLICATIONS

Examiner's report dated Jul. 10, 2012 issued in corresponding Japanese Patent Appln. No. 2009-124780.
Examiner's report dated Dec. 14, 2011 issued in corresponding Australian Patent Application No. 2009252215.
Examiner's report dated Jun. 11, 2012 issued in corresponding Korean Patent Appl. No. 10-2010-7026629.
Office Action dated Mar. 2, 2012 for corresponding Russian Application No. 201047886/14(069141).
L. Hao et al., "Effects of CO2 Laser Irradiation on the Wettability and Human Skin Fibroblast Cell Response of Magnesia Partially Stabilised Zirconia", Materials Science and Engineering C23 (2003) pp. 627-639.
L. Hao et al., "Correlation of the Hydroxyl Bond and Wetability Characterisitics of a Magnesia Partially Stabilised Zirconia Following CO2 Laser Irradiation", Thin Solid Films 468 (2004), pp. 12-16.
Jonathan P. Parry, et al., "Nanosecond-Laser Postprocessing of Millisecond-Laser-Machined Zirconia (Y-TZP) Surfaces", Int. J. Appl. Ceram. Technol., 5[3], 2008, pp. 249-257.
Examiner's report dated Aug. 8, 2012 issued in corresponding Swedish Patent Application No. 1051232-5.
Canadian Office Action issued on Sep. 10, 2012 in corresponding Canadian patent application No. 2,725,890.
Sergo et al., "Mechanical and chemical consequences of the residual stresses in plasma sprayed hydroxyapatite coatings", Biomaterials, vol. 18, No. 6, 1997, pp. 477-487.
Chemistry Unabridged Dictionary 5, 1979, pp. 25 right column to pp. 26 left column.
Examiner's report issued in corresponding Japanese patent application No. 2009-124780 on Nov. 22, 2012.
Japanese Office Action issued in corresponding application No. 200980119528.8 on Sep. 13, 2013.
R. W. Rice, Comparison of physical property-porosity behavior with minimum solid area models. Journal of Material Science 31 (1996), pp. 1509-1528—http://link.springer.com/article/1 0.1 007%2FBF00357860#.
Mech. and chem. consequences of the residual stresses in plasma sprayed hydroxyapatite coatings by V. Sergo, O. Sbaizeroa, D. R. Clarke—Pub. Mar. 1997—Dipartimento di Ingegneria dei Materiali, Universita di Trieste, Italy—Materials Department, University of California at San—http://www.sciencedirect.com/science/article/pii/S0142961296001470.
Pressureless Sintering and Mechanical and Biological Properties of Fluor-hydroxyapatite Composites with Zirconia by Hae-Won Kim, Young-Min Kong, Young-Hag Koh and Hyoun-Ee Kim—Pub. 2003—Intellectual Biointerface Engineering Center and College of Dentistry, Seoul National University, Seoul 110-749, Korea—http://slim.snu.ac.kr/pdf/110.pdf.
International Search Report for Application No. PCT/JP2009/060303 mailed Jun. 30, 2009.

* cited by examiner

IMPLANT BODY, METHOD OF MANUFACTURE OF SAME, AND DENTAL IMPLANT

TECHNICAL FIELD

The present invention relates to an implant body fixed in a tightly attached configuration to bone, for example, an implant body embedded in the bone of the jaw or the like when damage has occurred to the tooth root of a permanent tooth. The invention also relates to a method of manufacture for the implant body, and to a dental implant.

BACKGROUND

Conventionally, an implant body may be embedded into the bone and fixed in a contact configuration for application as an artificial bone, a bone attachment material, a bone reinforcing material, or the like.

For example, when a tooth root of a permanent tooth is destroyed by tooth decay or damage, a dental implant is used in which an implant body is inserted into a drill hole in the alveolar bone, and is fixed thereto. The dental implant is generally configured from an implant body that is fixed to the alveolar bone, and an abutment that is threadably attached to the implant body to thereby enable detachable mounting of an artificial dental crown.

The material currently employed to configure the implant body is often pure titanium. However since use of pure titanium entails the disadvantage of the risk of the occurrence of metal allergies or the attachment of bacteria, in recent years, ceramic materials that exhibit superior bio-affinity and mechanical strength have been examined as alternative materials adapted for an implant body. For example, Patent Literature 1 discusses several materials including a ceramic material as a material for an implant. Furthermore Japanese Patent Application Laid-Open No. 4046213 discloses the chemical, electrical, mechanical, laser processing or the like to create surface roughness on the surface of the implant in order to impart biocompatibility.

SUMMARY

The following problems remain unsolved in the conventional technique.

In other words, in the technique disclosed in Japanese Patent Application Laid-Open No. 4046213, although the biocompatibility is improved by roughening of the surface by the application of a mechanical process, laser process or the like to the surface of the implant, simple roughening is insufficient, and acquisition of improved bio-affinity and high levels of bone attachment is difficult. As a result, there is a need for an implant body that is provided with improved bio-affinity and that enables strong bone attachment, and in particular, there is a demand for an implant body that is formed by a ceramic material that has superior bio-affinity, mechanical strength, and the like.

The present invention is proposed in light of the above problems, and has the object of providing an implant body, a method of manufacture for the same, and a dental implant that enables improved bio-affinity and that enables strong bone attachment.

The present invention adopts the following configuration in order to solve the above problem. In other words, the implant body according to the present invention is an implant body that is fixed in a contact configuration to the bone, and is characterized in a configuration of a base material formed from zirconia, and a surface layer formed on the surface of the base material and having a lower hardness than the base material.

Since the implant body includes the base material formed from zirconia, and the surface layer formed on the surface of the base material and having a lower hardness than the base material, in addition to having superior mechanical strength due to the zirconia base material, the soft and flexible surface layer functions as a buffer layer to mitigate the difference in the degree of hardness between the bone and the base material, and therefore the soft surface further improves the bone adhesion characteristics.

The implant body according to the present invention is characterized by the formation of a plurality of crack cavities on the surface layer. In other words, since the implant body forms a plurality of crack cavities on the surface layer, rather than simple roughening, the bone cells can enter into the crack cavities in the surface layer. When the bone cells enter, the contact surface area is greatly increased, and a cross-linking effect is obtained. Furthermore high bone adhesion characteristics and bone attachment are obtained.

Furthermore the implant body according to the present invention is characterized in that the hardness of the surface layer is less than or equal to the hardness of the bone. In other words, since the hardness of the surface layer in the implant body is less than or equal to the hardness of the bone, attachment of bone tissue is facilitated by the flexible surface which has the same hardness as the bone or is softer than the bone.

Furthermore the surface layer of the implant body according to the present invention is characterized in being formed by zirconia hydroxide. In other words, since the surface layer of the implant body is formed by zirconia hydroxide, high bone adhesion characteristics and an improved bio-affinity with bone tissue are obtained by a zirconia hydroxide surface layer. In other words, the zirconia hydroxide surface layer is thought to have an ion exchange action and strengthens the increase in calcium ions and migration of cells to thereby obtain a considerable improvement in bone adhesion.

The dental implant according to the present invention is characterized by provision of the implant body according to the present invention that is inserted in a drill hole in the alveolar bone that acts as the bone, and is fixed thereto. That is to say, since the dental implant is provided with the implant body according to the present invention that is inserted and fixed in a drill hole in the alveolar bone, superior mechanical strength is obtained, and high bone adhesion to the alveolar bone is obtained by the soft flexible surface layer.

The method of manufacturing the implant body according to the present invention is a manufacturing method for the implant body that is fixed in a contact configuration to the bone. The method is characterized by including a step of forming a zirconia hydroxide surface layer having a lower hardness than the base material on the surface of the zirconia base material by irradiation of laser light in air including water vapor.

In other words, in the method of manufacturing the implant body, since the zirconia hydroxide surface layer having a lower hardness than the base material is formed on the surface of the base material formed from zirconia by irradiation of laser light in air including water vapor, formation of soft surface layer of zirconia hydroxide having a high adhesion is facilitated on the base material surface. In other words, the zirconia of the base material is irradiated with short-wavelength laser light such as solid-state laser light, and undergoes surface roughening by changing the surface configuration due to the high-energy laser light. In addition, the water vapor reacts with the zirconia to thereby enable formation of a hydroxide substance, in other words, a hydroxide (zirconium hydroxide) surface layer. Furthermore the zirconia hydroxide surface layer resulting from the manufacturing method enables a reduction in the level of hardness due to the production of a plurality of crack cavities.

The method of manufacturing of the implant body according to the present invention is characterized in that the laser light is laser light that has a fundamental wave caused by an Nd:YAG laser or a YVO$_4$ laser. In other words, since the method of manufacturing of the implant body uses laser light having a fundamental wave caused by an Nd:YAG laser or a YVO$_4$ laser, a zirconium hydroxide surface layer is formed on the zirconium base material surface by short-wavelength high-energy laser light, and facilitates formation of a plurality of crack cavities.

The manufacturing method for an implant body according to the present invention is characterized in that the hardness of the surface layer is less than or equal to the hardness of the bone as a result of irradiation with the laser light. In other words, in the manufacturing method for an implant body, since the hardness of the surface layer is less than or equal to the hardness of the bone as a result of irradiation with the laser light, as shown above, a surface layer is obtained in which attachment of bone tissue is facilitated.

The present invention obtains the following effect.

In other words, since the implant body according to the present invention, and the manufacturing method therefor, forms a surface layer that has a lower hardness than the base material on the surface of the base material formed from zirconia, in addition to mechanical strength that is superior to the zirconia base material, the soft and flexible surface layer functions as a buffer layer to mitigate the difference in the degree of hardness between the bone and the base material, and therefore the soft surface further improves the bone adhesion characteristics. Therefore the implant body obtains improved bio-affinity and high bone attachment. In particular, high bone attachment characteristics are obtained with respect to alveolar bone by application of the implant body of the dental implant that inserts and fixes the implant body to the drill hole in the alveolar bone.

DETAILED DESCRIPTION

Hereafter a first embodiment of the implant body, the method of manufacturing the same, and the dental implant according to the present invention will be described below making reference to FIG. 1 and FIG. 2.

Figure 1:
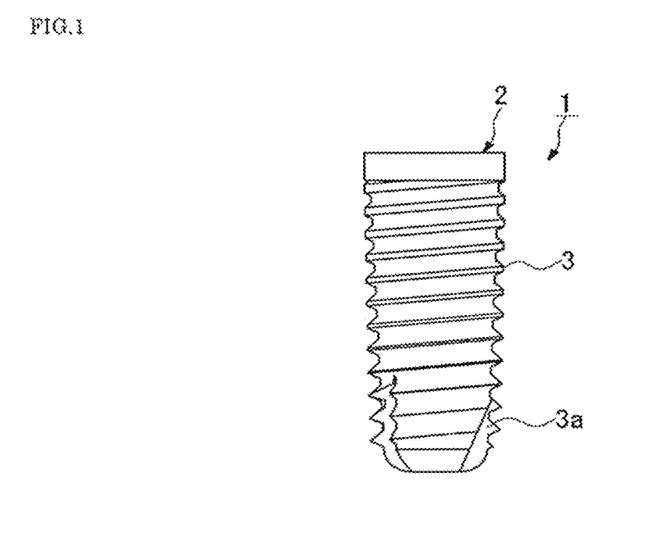
FIG. 1 is a front view showing a dental implant according to a first embodiment of an implant body, a method of manufacturing the same, and a dental implant according to the present invention.

The implant body 2 according to the present embodiment is an implant body fixed in a contact configuration to the bone, and as shown in FIG. 1, is applied to an implant body for a dental implant 1 inserted and fixed to a drill hole in alveolar bone that acts as the bone described above.

The implant body 2 is formed substantially in a cylindrical shape with a tip that has a gradually reducing external diameter towards a lower portion (distal end). The outer periphery of the implant body 2 forms as a male threaded portion 3. The male threaded portion 3 is formed by gradually varying the shape with respect to the axial direction of the implant body 2. The male threaded portion 3 is configured as a self-tapping threaded portion 3a in which the distal end is provided with an engraved groove on the thread, and thereby enables direct threadable engagement in the drilled hole of the alveolar bone.

An abutment (not shown) can be fixed by a bonding means such as a threaded structure to an upper portion of the implant body 2. For example, the male thread is formed on the lower portion of the abutment, and a female threaded hole (not shown) enabling threadable engagement with the male thread of the lower portion of the abutment is formed on the upper portion of the implant body 2.

Figure 2:
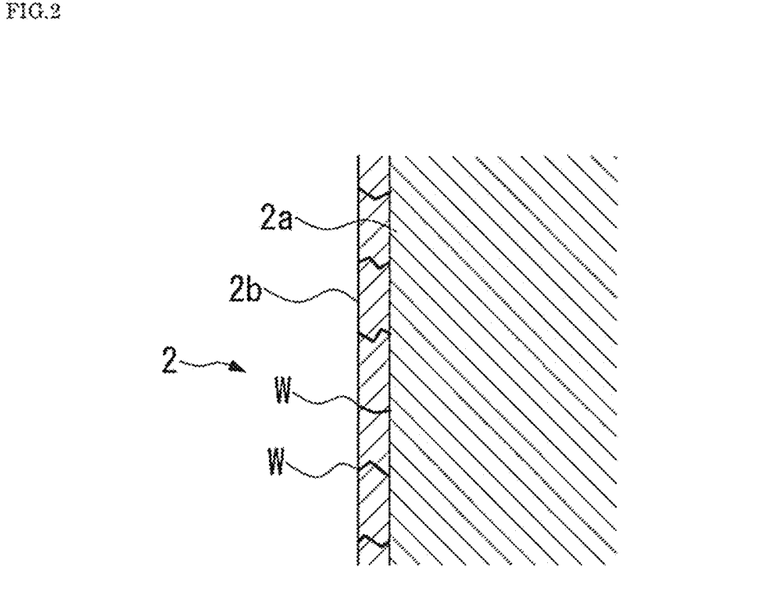
FIG. 2 is a schematic enlarged sectional view showing an implant body according to the present invention.

The implant body 2 as shown in FIG. 2 is configured from a base material 2a formed from zirconia and a surface layer 2b formed on the surface of the base material 2a from zirconia hydroxide having a hardness that is lower than the base material 2a.

A plurality of crack cavities W is formed on the surface layer 2b, and therefore further reduces the surface hardness.

The hardness of the surface layer 2b is less than or equal to the hardness of the alveolar bone. The hardness of the surface layer 2b in the present embodiment is of the level of 300 Hv in contrast to a Vickers hardness of the level of 500 Hv in normal alveolar bone.

Next, the method of manufacturing the implant body 2 of the dental implant will be described.

Firstly, a base material 2a of the implant body 2 that has an outer configuration including a male threaded portion 3 is prepared using zirconia (zirconia ceramic).

Next, a surface layer 2b of zirconia hydroxide is formed on the surface of the base material 2a by irradiating laser light in air containing moisture (in an atmosphere containing water vapor). The laser light that is employed at this time must be high-energy laser light, and for example, laser light (fundamental wave) produced by a Nd:YAG laser or a $YVO_4$ laser which are solid-state lasers is used.

When irradiating the laser light, a setting is adapted so that the hardness of the surface layer 2b is less than or equal to the hardness of the alveolar bone. In other words, since the Vickers hardness of alveolar bone is normally of the level of 500 Hv, in the present embodiment, the output or the like of the Nd:YAG laser light or the $YVO_4$ laser light is set and irradiated so that a surface layer having a hardness of substantially 300 Hv is formed. A blackened surface layer 2b is formed by irradiation of laser light.

Since the implant body 2 and the dental implant 1 provided with the implant body 2 according to the present embodiment are provided with a base material 2a that is formed from zirconia and a surface layer 2b that has a lower hardness than the base material 2a and is formed on the surface of the base material 2a, in addition to mechanical strength that is superior to that of the zirconia base material 2a, the soft and flexible surface layer 2b functions as a buffer layer to mitigate the difference in the degree of hardness between the bone such as alveolar bone and the base material 2a. Furthermore the bone adhesion characteristics are improved by the soft surface.

In particular, since a plurality of crack cavities W is formed on the surface layer 2b, rather than simple roughening, the bone cells can enter into the crack cavity W of the surface layer 2b. Entry of the bone cells causes a considerable increase in the contact surface area, obtains a cross-linking effect, and enables high bone adhesion and bone attachment.

In other words, an implant having a surface formed from a dense high-hardness ceramic material as in the conventional example exhibits an upper limit to improvement in bone adhesion that is enabled by simply roughening the surface. However in the implant body 2 according to the present embodiment, the hardness of the surface layer 2b is reduced by the plurality of crack cavities W formed in the surface and the bone cells can enter into an inner portion through the crack cavities W. Thus when the bone cells enter, high bone adhesion and bone attachment are enabled due to the increase in the contact surface area and the cross-linking effect.

Since the hardness of the surface layer 2b is less than or equal to the hardness of the bone such as alveolar bone, a hardness that is equivalent to bone such as alveolar bone or a surface that is softer and more flexible than bone such as alveolar bone facilitates improved close adhesion of bone tissue.

Furthermore, since the surface layer 2b is formed from zirconia hydroxide, superior bio-affinity and high bone attachment to bone tissue are enabled by the zirconia hydroxide of the surface layer 2b. In other words, the zirconia hydroxide of the surface layer 2b has an ion exchange effect which is thought to increase calcium ions and strengthen the growth of cells, and cause a considerable improvement in bone adhesion.

Since the method of manufacturing the implant body 2 forms a surface layer 2b of zirconia hydroxide having a lower hardness than the base material 2a on the surface of the zirconia base material 2a by irradiating laser light in air containing moisture, formation of a soft zirconia hydroxide surface layer 2b having high adhesion characteristics on the surface of the base material 2a can be facilitated. In other words, the surface configuration of the zirconia of the base material 2a that is irradiated with short-wave laser light such as a solid-state laser or the like undergoes roughening due to high energy laser light. However in addition, the zirconia reacts with the moisture to form a surface layer 2b of a hydroxide compound, in other words, a hydroxide (zirconia hydroxide).

The surface layer 2b of zirconia hydroxide formed by the method of manufacture has a reduced hardness due to the production of a plurality of crack cavities W.

In particular, laser light having a fundamental wave resulting from a Nd:YAG laser or a $YVO_4$ laser produces short-wavelength high-energy laser light and therefore forms a zirconia hydroxide surface layer 2b on the surface of the zirconia base material 2a and facilitates formation of the plurality of crack cavities W.

Next, the implant body, a method of manufacture for the implant body, and a dental implant according to the present invention will be described in detail by working examples making reference to FIG. 3 to FIG. 12.

Firstly a non-processed zirconia implant body without a hydroxide surface layer 2b processed using laser light as described above and formed from an unmodified zirconia base material 2a for the purposes of comparison, and a zirconia implant body processed by laser to form a hydroxide zirconia surface layer 2b using the laser light as described above as a working example were prepared. The irradiation laser light used an Nd:YAG laser as a fundamental wave.

Figure 3:
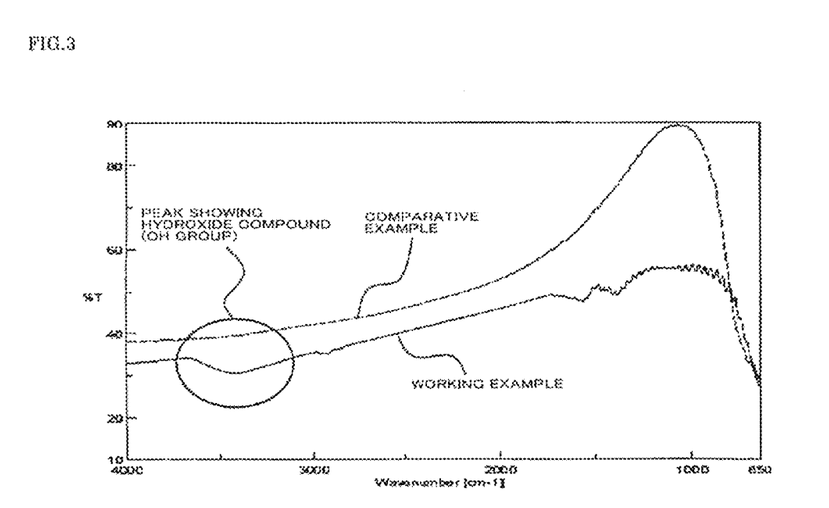
FIG. 3 is a graph shows the results of infrared spectrophotometric analysis of the surface according to a working example and a comparative example of an implant body, a method of manufacturing the same, and a dental implant according to the present invention.

The results obtained by application of infrared spectrophotometric analysis to the comparative example and the working example are shown in FIG. 3. The curved lines showing the comparative example and the working example in the figure are expressed with a vertical deviation for ease of comparison.

The result of this analysis show that the peak (falling portion of the curve) of the hydroxide compound (OH group) in the working example is observed in the portion enclosed by the circle in the figure, and that therefore zirconia hydroxide is formed as a hydroxide compound. In contrast, the comparative example of non-processed zirconia does not exhibit a hydroxide compound peak. Thus in the present working example, it is shown that a zirconia hydroxide surface layer 2b is formed by irradiation of laser light as described above on the surface of the zirconia base material 2a.

Next, the results of a hardness measurement using a nano-hardness tester (DLC film hardness measurement) are shown. A nano-hardness tester is a measurement apparatus that measures the load and the hardness, and is set to an engraved depth of 1 μm.

The results of two measurements of the Vickers hardness of the comparative example that is only formed from a zirconia base material 2a are 998 Hv and 1129 Hv. In contrast, the working example that forms a zirconia hydroxide surface layer 2b had a Vickers hardness of 336 Hv and 328 Hv. In other words, the hardness of the surface of the working example that forms a zirconia hydroxide surface layer 2b is clearly lower than the comparative example that is only formed from a zirconia base material 2a, and the surface is also soft in comparison to alveolar bone which normally has a hardness of the level of 500 Hv.

Figure 4:
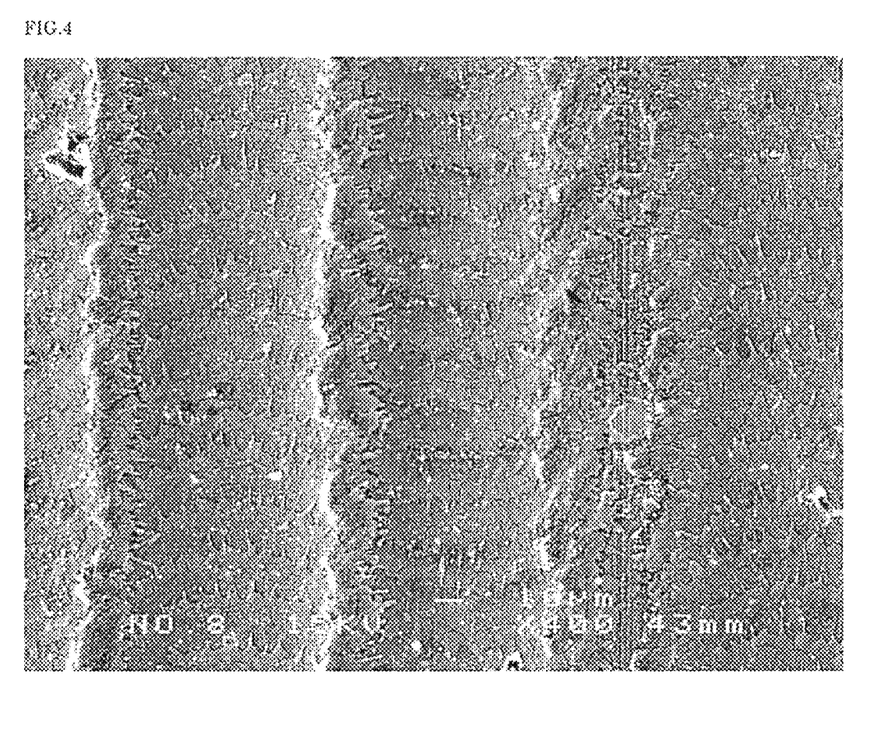
FIG. 4 is an SEM image of the surface of the implant body according to a working example of an implant body, a method of manufacturing the same, and a dental implant according to the present invention.
Figure 5:
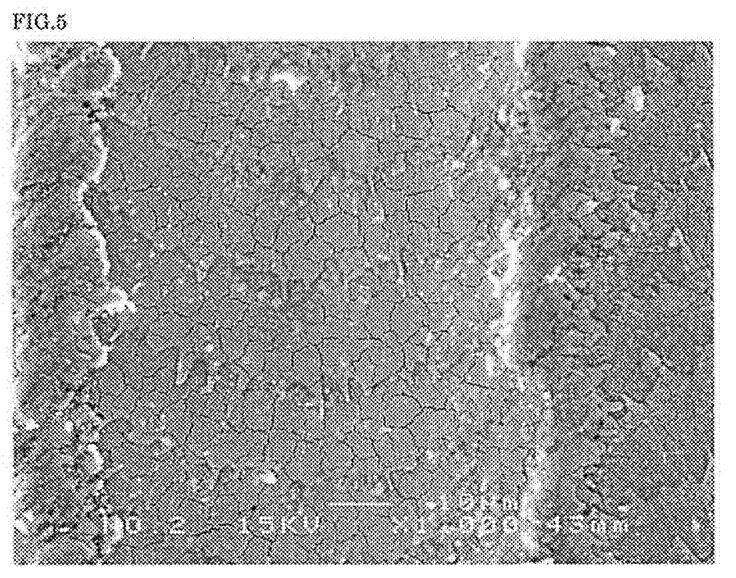
FIG. 5 is an SEM image of the surface of the implant body according to a working example of an implant body, a method of manufacturing the same, and a dental implant according to the present invention.
Figure 6:
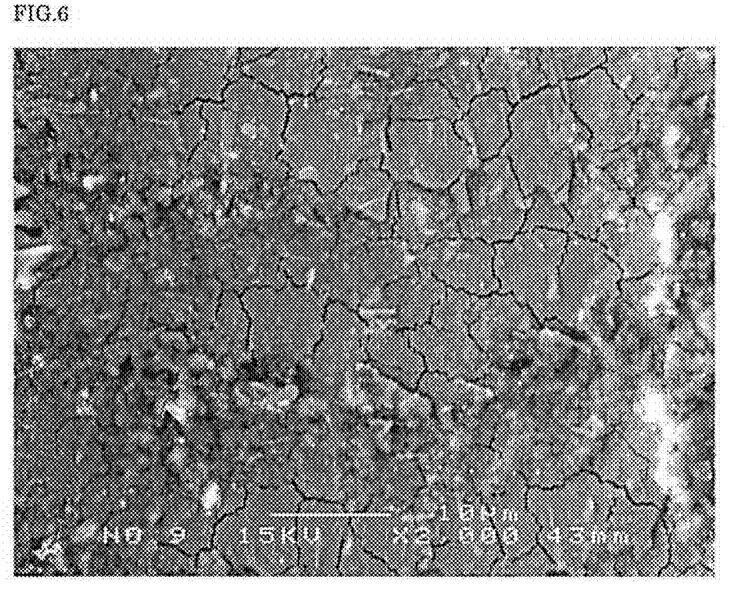
FIG. 6 is an SEM image of the surface of the implant body according to a working example of an implant body, a method of manufacturing the same, and a dental implant according to the present invention.

The surface layer 2b of the implant body 2 of the working examples is shown by SEM images captured using an electron microscope at different magnifications as shown in FIG. 4 to FIG. 6. As shown by these SEM images, a plurality of crack cavities W is produced in the surface layer 2b.

Next, the results observed in relation to the state four weeks after actually embedding the implant body in an experimental rat are shown in FIG. 7 to FIG. 12.

An implant body having a diameter of 1.6 mm and a length of 7.0 mm was used and embedded into the tibia of a four-week old SD rat. The implant body used in the present working example formed a surface layer due to irradiation with $YVO_4$ laser light.

Figure 7:
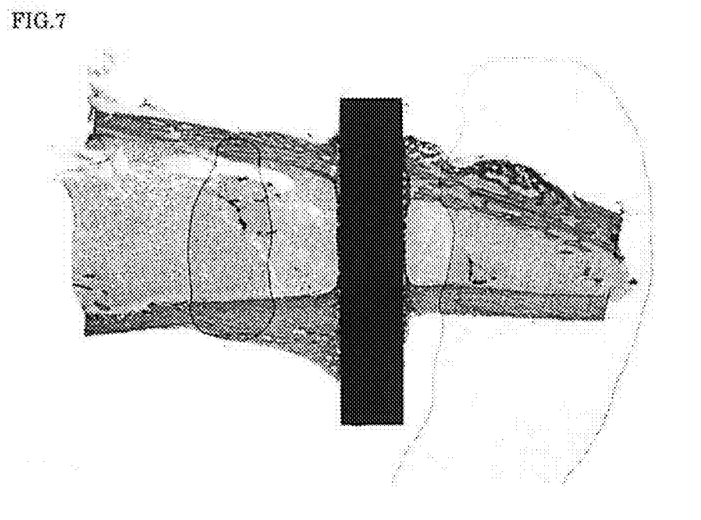
FIG. 7 is an enlarged photographic image of the principal sectional portions using an optical microscope 4 weeks after the insertion of an actual implant body into an experimental rat according to a comparative example of an implant body, a method of manufacturing the same, and a dental implant according to the present invention.
Figure 8:
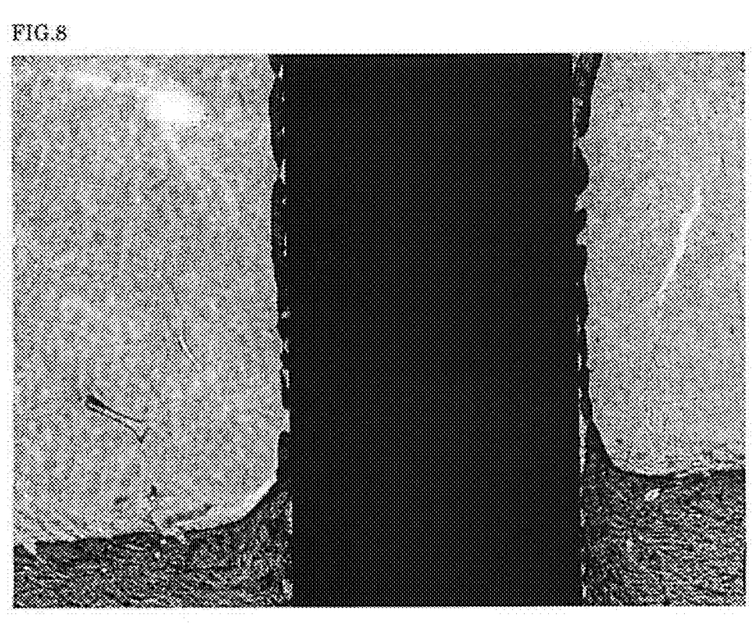
FIG. 8 is an enlarged photographic image of the principal sectional portions using an optical microscope 4 weeks after the insertion of an implant body into an experimental rat according to a comparative example of an implant body, a method of manufacturing the same, and a dental implant according to the present invention.
Figure 9:
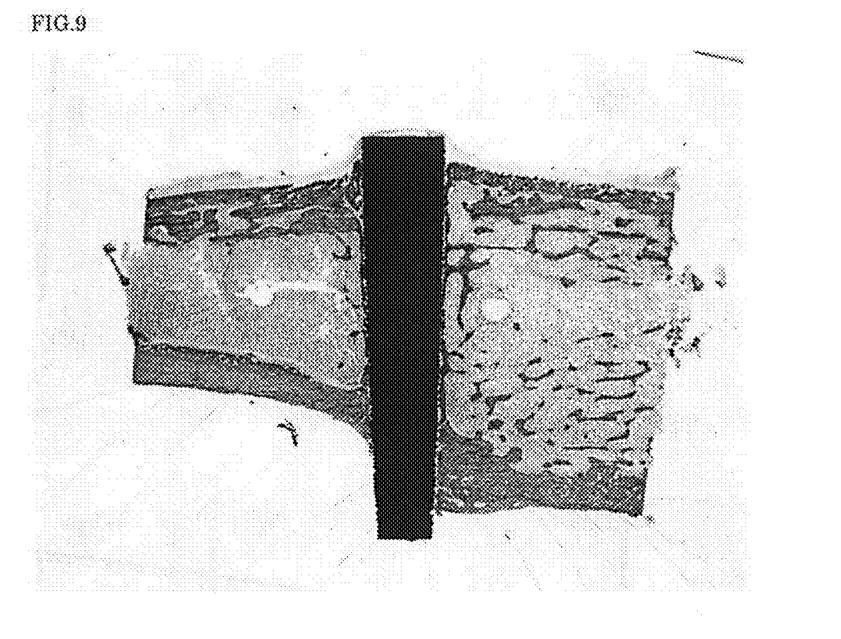
FIG. 9 is an enlarged photographic image of the principal sectional portions using an optical microscope 4 weeks after the insertion of an implant body into an experimental rat according to a working example of an implant body, a method of manufacturing the same, and a dental implant according to the present invention.
Figure 10:
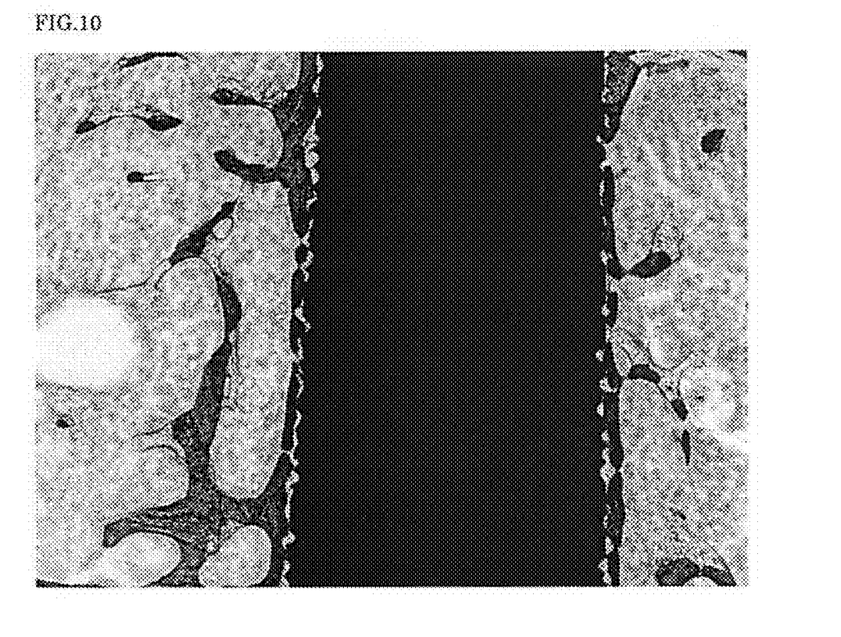
FIG. 10 is an enlarged photographic image of the principal sectional portions using an optical microscope 4 weeks after the insertion of an implant body into an experimental rat according to a working example of an implant body, a method of manufacturing the same, and a dental implant according to the present invention.
Figure 11:
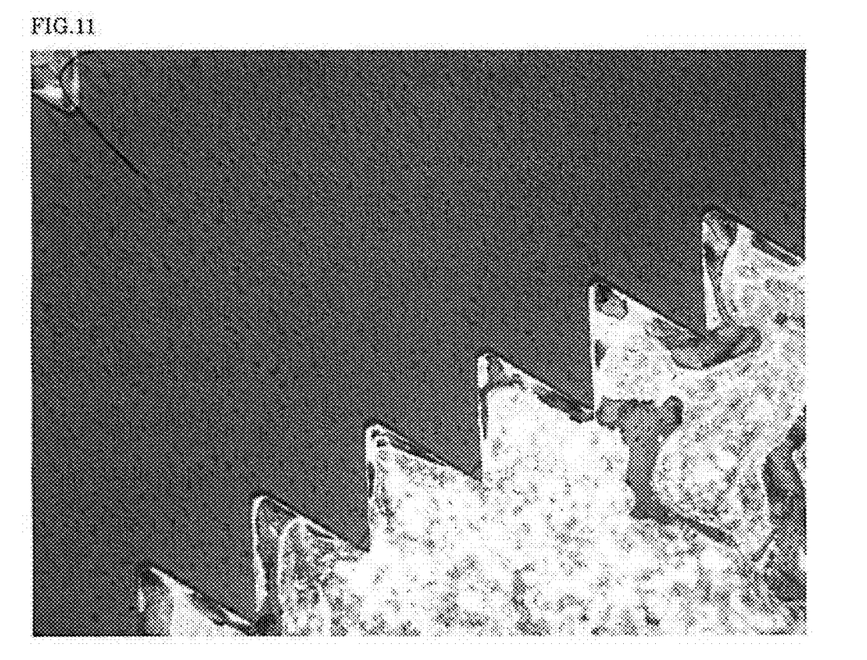
FIG. 11 is an enlarged photographic image of the principal sectional portions using an optical microscope 4 weeks after the insertion of an implant body into an experimental rat according to a comparative example of an implant body, a method of manufacturing the same, and a dental implant according to the present invention
Figure 12:
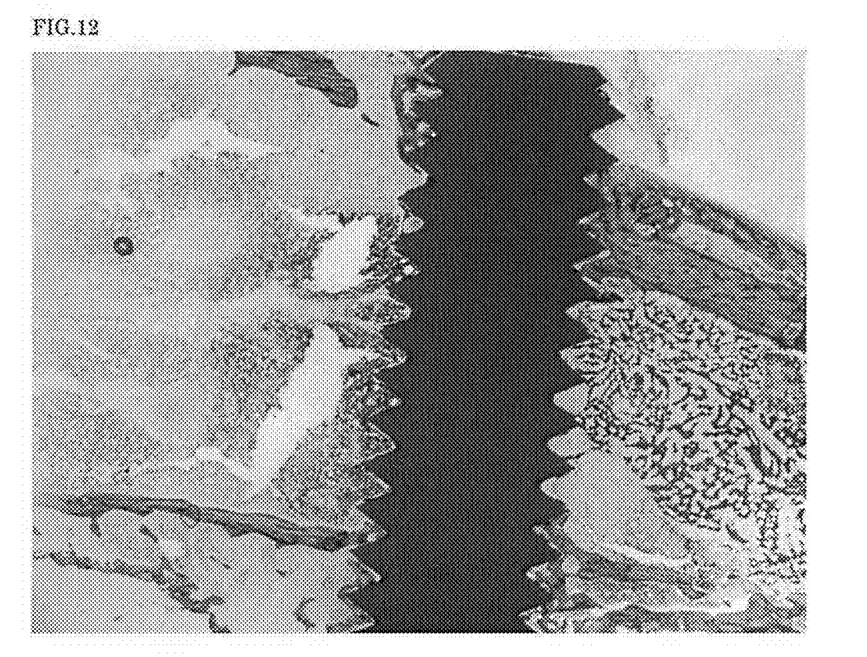
FIG. 12 is an enlarged photographic image of the principal sectional portions using an optical microscope 4 weeks after the insertion of an implant body into an experimental rat according to a working example of an implant body, a method of manufacturing the same, and a dental implant according to the present invention.

Firstly, FIG. 7, FIG. 8 and FIG. 11 are enlarged photographic images captured with an optical microscope of the principal sectional components when using the comparative example which only includes the zirconia base material 2a. The uniformly black section in the enlarged photographic images represents the implant body, and the partially black portion in the periphery thereof is a bone component that is dyed with toluidine blue (the original photographic images are color images, and the bone components are expressed as blue). In contrast, FIG. 9, FIG. 10 and FIG. 12 are enlarged photographic images captured using an optical microscope of the principal sectional components when using the working example which forms a zirconia hydroxide surface layer 2b. The magnifications used in the images are as follows: FIG. 7 is 10 times, FIG. 8 is 40 times, FIG. 9 is 10 times, FIG. 10 is 40 times, FIG. 11 is 150 times, and FIG. 12 is 50 times.

In the comparative example and the working example, the results of calculating the contact ratio between the surface of the implant body and the bone tissue results in a contact ratio for the comparative example of 27.9% in contrast to a contact ratio for the embodiment of 64.8% which therefore represents a considerable improvement in the contact ratio.

In this manner, in comparison to using the implant body according to the comparative example, a large amount of newly formed bone component is observed in the periphery of the implant body when using the implant body according to the working example, and it is shown that superior bio-affinity and high bone attachment are obtained. The regenerated bone in the periphery of the implant body comes into direct contact with the implant body and therefore achieves so-called ossointegration.

The technical scope of the present invention is not limited to the above embodiments and various modifications may be added without departing from the spirit of the present invention.

For example, in the present embodiment, although laser irradiation was performed using laser light produced by an Nd:YAG laser or a $YVO_4$ laser, another type of laser light may be employed to the degree that it is high-energy laser light that enables formation of a zirconia hydroxide surface layer 2b by hydroxide formation on the surface of the zirconia base material 2a. For example, laser light from another solid-state laser or laser light from a harmonic wave.

In the present embodiment, the implant body according to the present invention is applied as an implant body for a dental implant forming an artificial tooth root fixed by insertion into a drill hole in the alveolar bone. However the implant body may be applied as an implant body that is embedded or the like into bone in another region and fixed in a state of contact. For example, the implant body according to the present invention may be applied as artificial bone or a bone filling material in relation to damage to bone resulting from fracture or removal of benign tumors, or to supplement cartilage that is removed due to lumbar vertebrae surgery. Furthermore the implant body according to the present invention may be employed in relation to a member for an artificial joint, a bone attachment material used to fix positions of bone fracture, or a vertebral fixing apparatus.

What is claimed:

1. A method of manufacturing an implant body adapted to be fixed in a contact configuration to a bone, comprising:
    forming a zirconium hydroxide surface layer on a zirconia base material by irradiation of laser light, the surface layer formed by a reaction of the zirconia of the base material and moisture, wherein the surface layer has a lower hardness than the zirconia base material.

2. The method according to claim 1, wherein the laser light is a solid state laser.

3. The method according to claim 1, wherein the laser light is laser light having a fundamental wave caused by an Nd:YAG laser.

4. The method according to claim 1, wherein the hardness of the surface layer is less than or equal to the hardness of the bone as a result of irradiation with the laser light.

5. The method according to claim 1, wherein the laser light is laser light having a fundamental wave caused by a $YVO_4$ laser.

6. The method according to claim 1, wherein the forming step includes forming a plurality of crack cavities on the surface layer to improve bone adhesion.

7. A method of manufacturing an implant body, comprising:
    providing a base material formed from zirconia;
    irradiating the base material in the presence of water vapor with a laser light; and
    forming a zirconium hydroxide surface layer on the zirconia base material, wherein the surface layer has a lower hardness than the zirconia base material.

8. The method according to claim 7, wherein the laser light is a solid state laser.

9. The method according to claim 7, wherein the laser light is laser light having a fundamental wave caused by an Nd:YAG laser.

10. The method according to claim 7, wherein the hardness of the surface layer is less than or equal to the hardness of the bone as a result of irradiation with the laser light.

11. The method according to claim 7, wherein the laser light is laser light having a fundamental wave caused by a $YVO_4$ laser.

12. The method according to claim 7, wherein the forming step includes forming a plurality of crack cavities on the surface layer to improve bone adhesion.

* * * * *